US00PP24445P2

(12) United States Plant Patent
Nazeyrollas

(10) Patent No.: US PP24,445 P2
(45) Date of Patent: May 13, 2014

(54) ***ABELIA* PLANT NAMED 'MINDUO1'**

(50) Latin Name: *Abelia×grandiflora*
Varietal Denomination: MINDUO1

(71) Applicant: Olivier Nazeyrollas, Beaufort en Vallee (FR)

(72) Inventor: Olivier Nazeyrollas, Beaufort en Vallee (FR)

(73) Assignee: Pépiniéres Minier, Beaufort-en Vallée (FR)

( * ) Notice: Subject to any disclaimer, the term of this patent is extended or adjusted under 35 U.S.C. 154(b) by 0 days.

(21) Appl. No.: 13/573,616

(22) Filed: Sep. 27, 2012

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Kent L Bell
(74) *Attorney, Agent, or Firm* — C.A. Whealy

(57) ABSTRACT

A new and distinct cultivar of *Abelia* plant named 'Minduo1', characterized by its compact plant habit; freely branching habit; dense and bushy growth habit; freely and continuous flowering habit; relatively large inflorescences; pale yellow and purple-colored flowers; and good garden performance.

2 Drawing Sheets

Botanical designation: *Abelia×grandiflora.*
Cultivar denomination: 'MINDUO1'.

BACKGROUND OF THE INVENTION

The present invention relates to a new and distinct cultivar of *Abelia* plant, botanically known as *Abelia×grandiflora* and hereinafter referred to by the name 'Minduo1'.

The new *Abelia* is a product of a planned breeding program conducted by the Inventor in La Ménitré, Maine et Loire, France. The objective of the breeding program was to develop new compact and freely flowering *Abelia* plants with attractive flower coloration.

The new *Abelia* plant originated from an open-pollination in July, 2005 of *Abelia×grandiflora* 'Minfest', not patented, as the female, or seed parent with an unknown selection of *Abelia×grandiflora*, not patented. The new *Abelia* plant was discovered and selected by the Inventor in July, 2007 as a single flowering plant within the progeny of the stated open-pollination in a controlled environment in La Ménitré, Maine et Loire, France.

Asexual reproduction of the new *Abelia* plant by semi-hardwood cuttings in a controlled greenhouse environment in La Ménitré, Maine et Loire, France since October, 2004 has shown that the unique features of this new *Abelia* plant are stable and reproduced true to type in successive generations of asexual reproduction.

SUMMARY OF THE INVENTION

Plants of the new *Abelia* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Minduo1'. These characteristics in combination distinguish 'Minduo1' as a new and distinct cultivar of *Abelia* plant:

1. Compact plant habit.
2. Freely branching habit; dense and bushy growth habit.
3. Freely and continuous flowering habit.
4. Relatively large inflorescences.
5. Pale yellow and purple-colored flowers.
6. Good garden performance.

Plants of the new *Abelia* can be compared to plants of the female parent, 'Minfest'. In side-by-side comparisons, plants of the new *Abelia* differ primarily from plants of 'Minfest' in the following characteristics:

1. Plants of the new *Abelia* are more vigorous than plants of 'Minfest'.
2. Plants of the new *Abelia* are more freely branching than plants of 'Minfest'.
3. Plants of the new *Abelia* are more freely flowering than plants of 'Minfest'.
4. Plants of the new *Abelia* and 'Minfest' differ in leaf color as plants of 'Minfest' have variegated leaves.
5. Plants of the new *Abelia* and 'Minfest' differ in flower color as plants of 'Minfest' have lilac pink-colored flowers.

Plants of the new *Abelia* can be compared to plants of *Abelia×grandiflora* 'Edward Goucher', not patented. In side-by-side comparisons plants of the new *Abelia* differ from plants of 'Edward Goucher' in the following characteristics:

1. Plants of the new *Abelia* are more compact than plants of 'Edward Goucher'.
2. Plants of the new *Abelia* are more freely branching than plants of 'Edward Goucher'.
3. Plants of the new *Abelia* are more densely foliated and bushier than plants of 'Edward Goucher'.
4. Plants of the new *Abelia* have smaller and lighter green-colored leaves than plants of 'Edward Goucher'.
5. Plants of the new *Abelia* are more freely flowering than plants of 'Edward Goucher'.
6. Plants of the new *Abelia* and 'Edward Goucher' differ in flower color as plants of 'Edward Goucher' have lilac pink-colored flowers.

BRIEF DESCRIPTION OF THE PHOTOGRAPHS

The accompanying colored photographs illustrate the overall appearance of the new *Abelia* plant showing the colors as true as it is reasonably possible to obtain in colored reproductions of this type. Colors in the photographs may differ slightly from the color values cited in the detailed botanical description which accurately describe the colors of the new *Abelia* plant.

The photograph on the first sheet is a side perspective view of a typical plant of 'Minduo1' grown in an container.

The photograph on the second sheet is a close-up view of a typical flowering plant of 'Minduo1'.

DETAILED BOTANICAL DESCRIPTION

The aforementioned photographs and following observations, measurements and values describe plants grown in 15-liter containers during the spring and summer in a polyethylene-covered greenhouse in La Ménitré, Maine et Loire, France and under cultural practices which closely approximate commercial *Abelia* production. During the production of the plants, day temperatures averaged 19° C. and night temperatures averaged 13° C. Plants were five years old when the photographs and the description were taken. In the description, color references are made to The Royal Horticultural Society Colour Chart, 2001 Edition, except where general terms of ordinary dictionary significance are used.

Botanical classification: *Abelia×grandiflora* 'Minduo1'.

Parentage:

*Female, or seed, parent.*—*Abelia×grandiflora* 'Minfest', not patented.

*Male, or pollen, parent.*—Unknown selection of *Abelia×grandiflora*, not patented.

Propagation:

*Type.*—By semi-hardwood cuttings.

*Time to initiate roots, summer.*—About 40 days at 18° C.

*Time to produce a rooted young plant, summer.*—About three months at 18° C.

*Root description.*—Fine, fleshy; white in color.

*Rooting habit.*—Moderate branching; low density.

Plant description:

*Plant form and growth habit.*—Perennial shrub; compact and rounded plant habit; moderate vigorous growth habit.

*Branching habit.*—Freely branching habit, dense and bushy growth habit with about 80 lateral branches develop per plant; pinching enhances lateral branch development.

*Plant height.*—About 60 cm to 80 cm.

*Plant diameter* (*area of spread*).—About 100 cm.

Lateral branch description:

*Length.*—About 60 cm.

*Diameter.*—About 3 mm.

*Internode length.*—About 3 cm.

*Aspect.*—Initially upright to arching outwardly.

*Texture, developing.*—Smooth, glabrous.

*Texture, fully developed.*—Woody.

*Color, developing.*—Close to 184A.

*Color, fully developed.*—Close to 197C.

Foliage description:

*Arrangement.*—Opposite, simple.

*Length.*—About 2.7 cm.

*Width.*—About 1.2 cm.

*Shape.*—Ovate.

*Apex.*—Acuminate.

*Base.*—Obtuse.

*Margin.*—Serrate.

*Texture, upper and lower surfaces.*—Smooth, pubescent.

*Venation pattern.*—Pinnate.

*Color.*—Developing leaves, upper surface: Close to 143A. Developing leaves, lower surface: Close to 143C. Fully expanded leaves, upper surface: Close to 137A; venation, close to 141C. Fully expanded leaves, lower surface: Close to 138A; venation, close to 138A.

*Petiole.*—Length: About 2 mm. Diameter: About 0.5 mm. Texture, upper and lower surfaces: Smooth, glabrous. Color, upper surface: Close to 137C. Color, lower surface: Close to 138A.

Flower description:

*Flower appearance and arrangement.*—Single funnel-form flowers arranged on terminal and axillary panicles; freely flowering habit with about 50 flowers developing per lateral branch; flower face mostly outwardly.

*Inflorescence height.*—About 28.8 cm.

*Inflorescence width.*—About 8.3 cm.

*Fragrance.*—Fragrant, spicy.

*Flower longevity.*—Flowers last for about two weeks on the plant; flowers not persistent.

*Natural flowering season.*—Long flowering period, plants flower continuously from June to September in France.

*Flower diameter.*—About 1.5 cm.

*Flower depth.*—About 2 cm.

*Flower buds.*—Length: About 1.4 cm. Diameter: About 5 mm. Shape: Obovate. Color: Close to 9D and 77A.

*Petals.*—Quantity and arrangement: Five fused petals arranged in a single whorl. Lobe length: About 5 mm. Lobe width: About 4 mm. Shape: Roughly spatulate. Apex: Obtuse. Margin: Entire. Texture, upper and lower surfaces: Smooth, glabrous. Color: When opening, upper surface: Close to 10C. When opening, lower surface: Close to 10D. Fully opened, upper surface: Close to 10D; throat, close to 10D and 77A; nectar guides, close to 23B. Fully opened, lower surface: Close to 10D; tube, close to 10D and 77C.

*Sepals.*—Quantity and arrangement: Two, opposite; calyx cruciform. Length: About 9 mm. Width: About 4 mm. Shape: Oblong. Apex: Obtuse. Base: Cuneate. Margin:. Entire. Texture, upper and lower surfaces: Smooth, glabrous. Color, developing, upper and lower surfaces: Close to N34C. Color, fully developed, upper and lower surfaces: Close to N34C.

*Peduncles.*—Length: About 20.8 cm. Diameter: About 2 mm. Strength: Strong, flexible. Texture: Smooth, glabrous. Angle: About 30° from lateral branch. Color: Close to 165B.

*Pedicels.*—Length: About 2 mm. Diameter: About 1 mm. Strength: Strong, flexible. Texture: Smooth, glabrous. Angle: Mostly upright. Color: Close to 143A.

*Reproductive organs.*—Stamens: Quantity per flower: Four. Anther length: About 2 mm. Anther shape: Oblong to elliptical. Anther color: Close to 155A. Pollen amount: Moderate. Pollen color: Close to 155A. Pistils: Quantity per flower: One. Pistil length: About 2.2 cm. Stigma shape: Globular. Stigma color: Close to 9D. Style length: About 2.1 cm. Style color: Close to 9D. Ovary color: Close to 155A. Seeds:

Length: About 0.6 mm. Diameter: About 0.1 mm. Color, immature: Green tinged with red. Color, mature: Brown.

Garden performance: Plants of the new *Abelia* have been observed to have good garden performance and to tolerate rain, wind and to tolerate temperatures ranging from −15° C. to 40° C.

Pathogen & pest resistance: Plants of the new *Abelia* have not been shown to be resistant to pathogens and pests common to *Abelia* plants.

It is claimed:

1. A new and distinct *Abelia* plant named 'Minduo1' as illustrated and described.

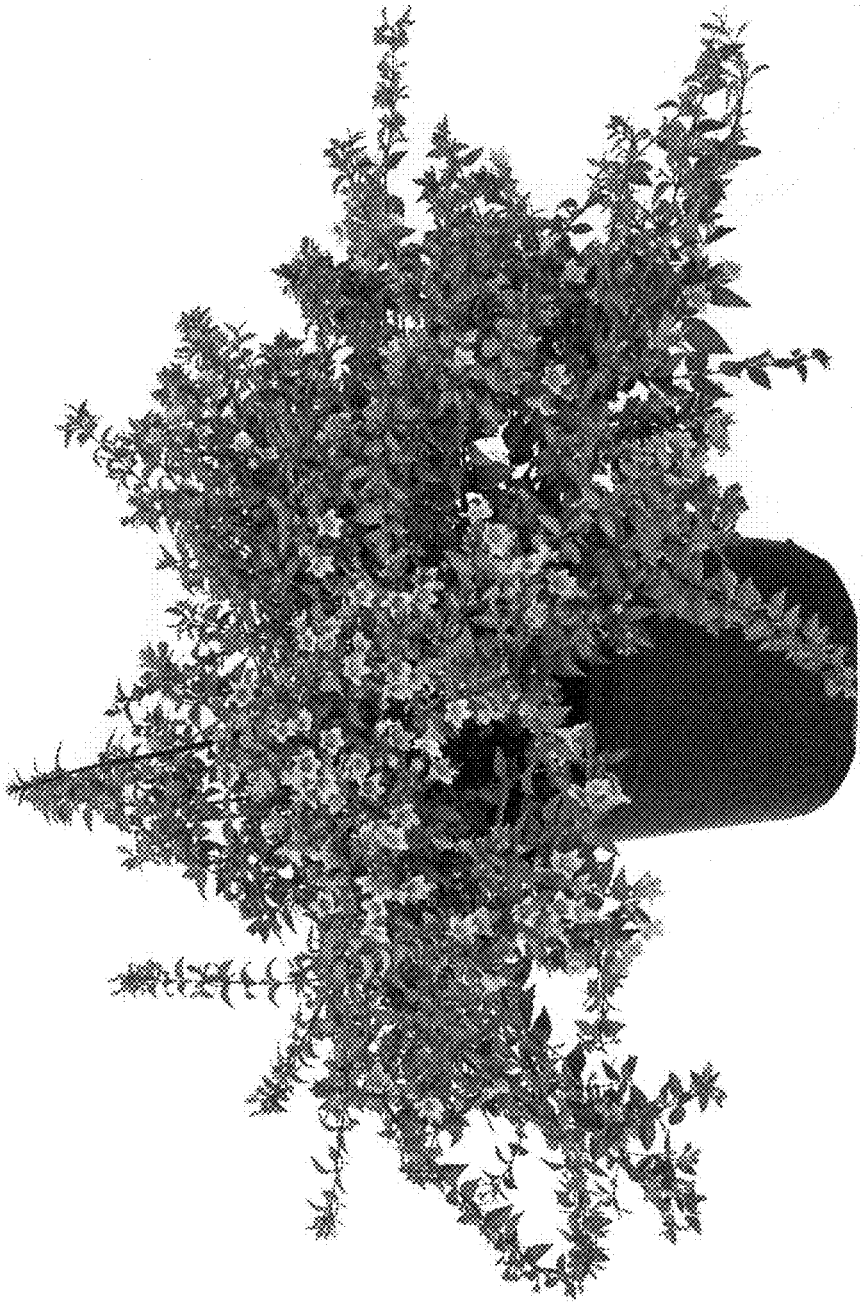

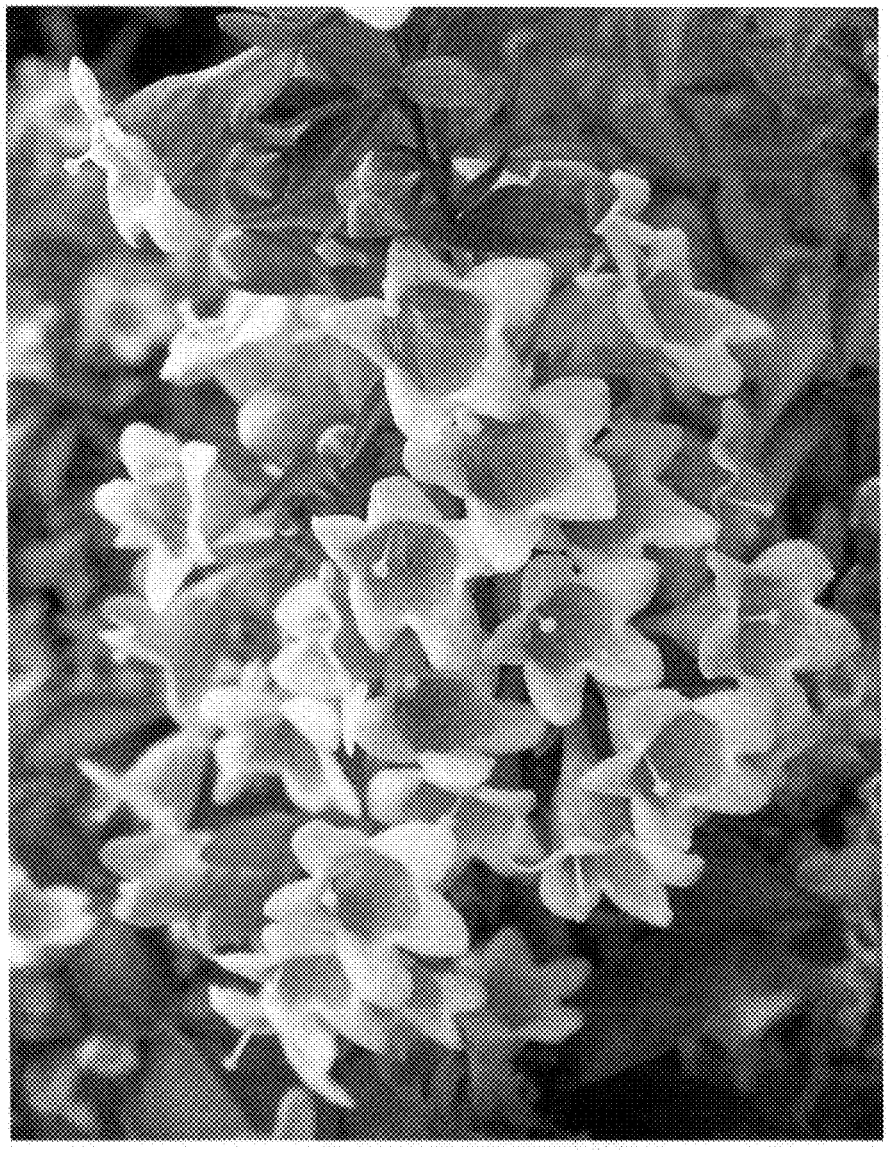

* * * * *